United States Patent [19]

O'Laughlin et al.

[11] Patent Number: 4,868,169

[45] Date of Patent: Sep. 19, 1989

[54] STEROID CREAM FORMULATION

[75] Inventors: Richard L. O'Laughlin, North Brunswick; Andrea Panaggio, Jamesburg; Sailesh A. Varia, Plainsboro, all of N.J.

[73] Assignee: E. R. Squibb & Sons, Inc., Princeton, N.J.

[21] Appl. No.: 120,278

[22] Filed: Nov. 13, 1987

[51] Int. Cl.$^4$ ............................................. A61K 31/56
[52] U.S. Cl. ................................... 514/179; 514/177; 514/178; 514/180
[58] Field of Search .................... 514/169, 170–179, 514/180–182, 937–941, 943, 944, 947, 969, 970, 973

[56] References Cited

U.S. PATENT DOCUMENTS

| | | | |
|---|---|---|---|
| 3,178,345 | 4/1965 | Schlagel | 514/171 |
| 4,361,559 | 11/1982 | Varma | 424/243 |
| 4,542,129 | 9/1985 | Orentreich | 514/178 |

*Primary Examiner*—H. M. S. Sneed
*Assistant Examiner*—J. Saba
*Attorney, Agent, or Firm*—Burton Rodney

[57] ABSTRACT

A steroid cream formulation which has enhanced physical and chemical stability is formed of $(11\beta,17\alpha)$-17-(ethylthio)-9α-fluoro-11β-hydroxy-17-(methylthio)androsta-1,4-dien-3-one (tipredane), and a vehicle containing as major ingredients glyceryl monostearate having an acid value of greater than 4, propylene glycol and water together with a sodium citrate or potassium citrate buffer, a non-acidic long chain fatty acid wax to impart proper consistency, and sodium metabisulfite as an antioxidant, together with emulsifiers, skin conditioners, emollients, lubricants and other conventional cream formulation ingredients.

14 Claims, No Drawings

STEROID CREAM FORMULATION

FIELD OF THE INVENTION

The present invention relates to a steroid cream formulation which has enhanced physical and chemical stability and contains (11β, 17α)-17-(ethylthio)-9α-fluoro-11'-hydroxy-17-(methylthio)androsta-1,4-dien-3-one (tipredane) as the active ingredient.

BACKGROUND OF THE INVENTION

U.S. Pat. No. 4,361,559 to Varma discloses antiinflammatory 17,17-bis(substituted thio)androstenes of the formula

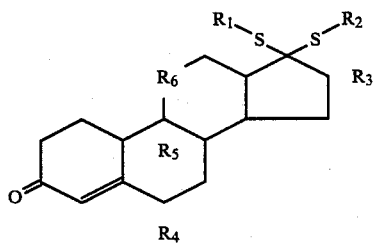

wherein $R_1$ and $R_2$ are the same or different and each is alkyl, cycloalkyl or aryl;

$R_3$ is hydrogen, hydroxy, alkoxy, aryloxy, alkylthio, arylthio,

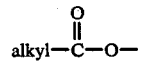

or halogen;

$R_4$ is hydrogen, methyl, hydroxy,

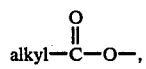

or halogen;

$R_5$ is hydrogen or halogen; and $R_6$ is carbonyl or β-hydroxymethylene. A broken line in the 1,2-, 6,7- and 15,16-position of a structural formula indicates the optional presence of ethylenic unsaturation.

Included among the compounds covered in the Varma patent is tipredane which has been found to be a highly effective topical antiinflammatory agent.

Tipredane is practically insoluble in water (less than 0.0002 mg/ml at 25° C.); 1:1 hydroalcoholic mixtures of tipredane are unstable under acidic conditions. Further, tipredane itself is susceptible to oxidation.

It is known to use monoglycerides such as glyceryl monostearate as a thickener in steroid cream formulations. For example, U.S. Pat. No. 3,892,857 to DiFazio et al discloses a cream formulation containing propylene glycol, water and a steroid, namely, 21-chloro-9α-fluoro-Δ⁴-pregnene-11β,16α,17α-triol-3,20-dione 16,17-acetonide (halcinonide) and as an oleaginous thickener monoglycerides such as glyceryl monostearate, glyceryl monooleate, glyceryl monopalmitate and glyceryl ricinoleate.

Where it has been attempted to employ generally commercially available glyceryl monostearate in an oil-in-water tipredane cream formulation, it has been found that syneresis of the aqueous phase occurs.

Another problem associated with formulating of oil-in-water tipredane creams is obtaining proper consistency without sacrificing chemical and physical stability of the tipredane.

DESCRIPTION OF THE INVENTION

In accordance with the present invention, a topical oil-in-water steroid cream formulation is provided which contains the steroid tipredane as its active ingredient and has excellent physical and chemical stability and does not undergo syneresis although it contains glyceryl monostearate. The oil-in-water cream formulation according to the present invention contains in addition to tipredane, a carrier vehicle which is formed of one or more solubilizers for the tipredane, water, one or more emulsifiers including glyceryl monostearate (which has an acid value of greater than 4), one or more buffers to impart a neutral or slightly alkaline pH, and preferably within the range of from about 5 to about 9, optionally one or more emollients, optionally one or more metal chelating agents, optionally one or more skin conditioners, optionally one or more preservatives, and optionally one or more silicone lubricants or defoaming agents.

In addition, in order to obtain acceptable consistency and chemical stability, the cream formulation of the invention will include a non-acidic long chain fatty acid ester wax to impart desired consistency to the cream so that the cream remains in solid form at temperatures as high as 40° C., such as Syncrowax ERLC (trademark of Croda) which is ethylene glycol ester of a long chain ($C_{18}$-$C_{36}$) fatty acid wax. It has been found that such non-acidic wax will impart the desired consistency to the cream but will not interfere with the stability of the tipredane.

The tipredane steroid will be employed in the form of a micronized powder having an average particle size of less than about 75 microns and will be present in an amount within the range of from about 0.005 to about 0.5% by weight and preferably from about 0.05 to about 0.3% by weight based on the total weight of the tipredane cream formulation to supply from about 0.5 to about 3 mg/g activity.

As indicated, the carrier vehicle will contain one or more solubilizers for the tipredane such as propylene glycol (which also serves as a preservative, lubricant, humectant and emollient), polysorbate 60, benzyl alcohol or mixtures thereof.

The propylene glycol and/or other solubilizers will be present in an amount within the range of from about 5 to about 30% by weight and preferably from about 10 to about 20% by weight of the cream formulation.

Water which serves as a vehicle for the cream formulation and a solubilizer for salts present in the formulation, will be present in an amount within the range of from about 30 to about 70% and preferably from about 40 to about 65% by weight of the total cream formulation.

An important feature of the cream formulation of the invention is its excellent chemical stability and physical stability. Syneresis will not occur if glyceryl monostearate having acid value of greater than 4 is used. However, if low acid value glyceryl monostearate is used, the cream will show syneresis initially, but if the bulk cream is stored for a period of 1 to 3 weeks, it firms up in consistency and syneresis no longer occurs. Further, low acid value glyceryl monostearate may be used, for example, acid value of 0.5 to 4, in which case stearic acid or other acid is employed in conjunction therewith to bring its acid value to greater than 4.

A buffer is included to impart a pH to the cream of within the range of from about 5 to about 9 and preferably from about 6.5 to about 8.5 so as to ensure chemical stability of the tipredane. Examples of buffers suitable for use herein include sodium citrate, potassium citrate in the form of the monohydrate, or an alkali metal hydroxide, such as sodium hydroxide or potassium hydroxide or magnesium hydroxide or aluminum hydroxide. It is preferred to use a mixture of buffers such as sodium citrate and aluminum hydroxide (2:1 to 0.5:1).

The cream formulation will include a thickener which is a non-acidic long chain fatty wax (as described above) in an amount within the range of from about 0.5 to about 5 weight % and preferably from about 1 to about 3 weight % based on the weight of total tipredane cream formulation. Examples of non-acid long chain fatty waxes suitable for use herein include, but are not limited to Syncrowax ERLC (described above), white wax, carnauba wax, paraffin wax or ceresin wax.

The emulsifier will be present in an amount within the range of from about 2 to about 8 weight 5 and preferably from about 3 to about 7 weight % based on the weight of the total tipredane cream formulation. Examples of emulsifiers suitable for use herein include but are not limited to polyethylene oxide 60 sorbitan monostearate (polysorbate 60), polysorbate 20, polysorbate 65, polysorbate 80, or Promulgen D (ceteary1 alcohol and ceteareth-20 (3:1)).

The cream formulation of the invention will also include an emulsion stabilizer such as glyceryl monostearate, cetyl alcohol or stearyl alcohol in an amount within the range of from about 5 to about 25% by weight, and preferably from about 7 to about 22% by weight. It is preferred to employ a mixture of such emulsion stabilizers such as, glyceryl monostearate in an amount of within the range of from about 5 to about 15% by weight and preferably from about 7 to bout 13% by weight, and cetyl alcohol in an amount within the range of from about 2 to about 8% by weight and preferably from about 3 to about 7% by weight.

All of the above % are based on the total weight of the tipredane cream formulation.

The emollients may be present in an amount within the range of from about 1 to about 6% and preferably from about 2 to about 4% by weight based on the total tipredane cream formulation. Examples of emollients suitable for use herein include but are not limited to mineral oil, lanolin alcohol, a mixture of mineral oil and lanolin alcohol (9:1) as sold under the trademark Amerchol L-101 (Amerchol Corp, a unit of CPC International). Examples of other emollients suitable for use herein include, but are not limited to cetyl alcohol, isopropyl isostearate, isopropyl myristate, isopropyl palmitate or octyl dodecyl stearate.

The cream formulation may optionally include one or more skin conditioners or humectants in an amount of within the range of from about 0.5 to about 4% and preferably from about 1 to about 3% by weight based on the total tipredane cream formulation, such as an alkoxylated methyl glucose derivative, for example, polypropylene glycol-20 methyl glucose ether (Glucam P-20, trademark of Amerchol Corp, CPC Int.), polypropylene glycol-10 methyl glucose ether (Glucam P-10, trademark of Amerchol Corp, CPC Int.) and polyethylene glycol ether of methyl glucose (Glucam E-10 or E-20). Other skin conditioners that may be employed include allantoin, d- or dl-panthenol, sodium 2-pyrrolidone carboxylic acid and the like.

In addition, the cream formulation will include a lubricant or defoamer in an amount within the range of from about 0.1 to about 3% by weight and preferably from about 0.5 to about 2% by weight based on the total tipredane cream formulation. Examples of such lubricants suitable for use herein include, but are not limited to silicones such as dimethicone (Silicone DC 200 Fluid (350 CS)), polyphenylmethylsiloxane or polydimethylsiloxane.

The cream formulation of the invention will include an antioxidant, such as sodium metabisulfite, butylated hydroxytoleuene, butylated hydroxyanisole or sodium ascorbate in an amount within the range of from about 0.01 to about 1% by weight and preferably from about 0.02 to about 0.5% by weight of the tipredane cream formulation.

As the optional chelating agent disodium or dipotassium ethylenediamine tetraacetate dihydrate is preferred. Other examples of metal chelating agents which may be employed include citric acid, fumaric acid or malic acid. The metal chelating agent will be employed in an amount within the range of from about 0.001 to about 0.5% by weight and preferably from about 0.002 to about 0.1% by weight of the tipredane cream formulation.

The following represents preferred oil-in-water cream formulations in accordance with the present invention.

| Ingredient | Range Percent w/w |
| --- | --- |
| Tipredane (in form of micronized powder) ($<75\mu$) | 0.05 to 0.3 |
| Glyceryl monostearate (emulsion stabilizer) | 7 to 13 |
| Propylene glycol (solubilizer-preservative) | 10 to 20 |
| Sodium citrate (buffer) | 0.3 to 0.7 |
| Sodium metabisulfite (antioxidant) | 0.02 to 0.5 |
| Disodium EDTA dihydrate (chelating agent) | 0.002 to 0.1 |
| Aluminum hydroxide conc. wet gel (buffer) | 0.10 to 0.60 |
| Syncrowax ERLC (non-acidic long chain fatty acid wax-thickener) | 1 to 3 |
| Cetyl alcohol (emulsion stabilizer) | 3 to 7 |
| Mineral oil-lanolin alcohol combination (9:1) (emollient) | 2 to 4 |
| Methyl gluceth-20 (skin conditioner) | 1 to 3 |
| Polysorbate 60 (emulsifer) | 3 to 7 |
| Silicone fluid (lubricant or defoamer) | 0.5 to 2 |
| Water | 40 to 65 |

The tipredane cream formulation of the invention may be prepared as described in the working Example by simply forming an aqueous phase (containing methyl gluceth-20, polysorbate-10, propylene glycol, sodium citrate, EDTA and sodium metabisulfite, aluminum hydroxide and silicone fluid) and an oil phase (containing glyceryl monostearate cetyl alcohol, mineral oil-lanolin alcohol, Syncrowax) and mixing the two phases until a homogeneous oil-in-water emollient cream is obtained.

The following Example represents a preferred embodiment of the present invention. Unless otherwise indicated, all temperatures are expressed in degrees Centigrade.

EXAMPLE

A 0.1% w/w tipredane oil-in-water formulation having the following composition was prepared as described below.

| Tipredane Cream 0.1 W/W | |
|---|---|
| Ingredient | Amount (mg) |
| Tipredane micronized powder (20μ) (to supply 1.0 mg/g activity) | 1 |
| Glyceryl monostearate (emulsion stabilizer) | 110 |
| Cetyl alcohol NF (emulsion stabilizer) | 40 |
| Syncrowax ERLC (Croda) (wax for proper consistency) | 15 |
| Amerchol L-101 (mineral oil and lanolin alcohol [9:1])(emollient) | 30 |
| Glucam E-20 (methyl gluceth-20)(skin conditioner) | 20 |
| Tween 60 (polysorbate 60)(emulsifier) | 40 |
| Propylene glycol USP (solubilizer-preservative) | 150 |
| Silicone DC200 fluid (350CS) (lubricant-defoamer) | 10 |
| Sodium citrate USP (buffer) | 5 |
| Disodium edetate dihydrate USP (chelating agent) | 0.05 |
| Sodium metabisulfite (antioxidant) | 0.2 |
| Aluminum hydroxide conc. wet gel (buffer) | 4 |
| Purified water USP (or equivalent) ca. sufficient quantity to make | 575 1 g |

A mixture of glyceryl monostearate and cetyl alcohol was heated to 60° to 65° to melt same. Syncrowax ERLC was added with agitation and the mixture was heated to 80° to 85° C. The mineral oil-lanolin alcohol (Amerchol L-101) was added with agitation and the so-formed oil phase was maintained at 80° to 85° C. until it was ready to add same to the aqueous phase.

The water phase was prepared by mixing methyl gluceth-20, polysorbate 60, propylene glycol (80% of total propylene glycol), sodium citrate, disodium edetate dihydrate and sodium metabisulfite with agitated purified water and heating to 80° to 85° C.

Aluminum hydroxide concentrated wet gel was added to a portion of purified water; the resulting slurry was passed through a colloid mill to form a smooth dispersion which was added to the above aqueous solution at 80° to 85° C.

The oil phase was heated at 90°-95° C. and added to the aqueous phase at 90°-95° C. with homogenization to form an oil in water emulsion. The batch was cooled to 70°-75° C. with continuous homogenization. Silicone fluid was added and the batch was cooled. The weight of the batch was adjusted with hot purified water (54°-56° C.) while maintaining continuous homogenization to prevent phase separation. The batch was cooled to about 50° C. to 52° C. or until onset of congealing. Homogenization was stopped and the batch was cooled to 25°-30° C. using planetary type mixing. A slow rate of cooling (not greater than 1° C. per 15 minutes) was used during congealing phase from 49° C. to 44° C. The batch was allowed to cool below 44° C. by standing overnight without mixing until cooled to 25°-30° C. Tipredane was dispersed in the remainder of the propylene glycol using a colloid mill homogenizer and added to the batch at 25°-30° C. The final batch weight was adjusted with purified water. The mix was mixed an additional 30 minutes until homogeneous.

The above tipredane cream formulation was found to have excellent chemical and physical stability and did not undergo syneresis even after prolonged periods of storage at temperatures of 5° C., 25° C. and 40° C.

What is claimed is:

1. A tipredane cream formulation having enhanced chemical and physical stability comprising tipredane in an amount within the range of from about 0.005 to about 0.5%, and a vehicle comprising a solubilizer for tipredane said solubilizer being present in an amount within the range of from about 5 to about 30%, water in an amount within the range of from about 30 to about 70%, at least one emulsifier which includes glyceryl monostearate having an acid value of greater than about 4 present in an amount within the range of from about 5 to about 25%, at least one buffer to impart a neutral or slightly alkaline pH, a nonacidic long chain fatty acid wax which imparts desired consistency to the cream formulation present in an amount within the range of from about 0.5 to about 5%, optionally one or more emollients which when present is in an amount within the range of from about 1 to about 6%, optionally one or more metal chelating agents which when present is in an amount within the range of from about 0.001 to about 0.5%, optionally one or more lubricants which when present is in an amount within the range of from about 0.1 to about 3%, optionally one or more antioxidants which when present is in an amount within the range of from about 0.01 to about 1%, and optionally one or more skin conditioners which when present is in an amount within the range of from about 0.5 to about 4%, all of the above % being based on the weight of the tipredane cream formulation.

2. The cream formulation as defined in claim 1 wherein the solubilizer for tipredane is propylene glycol.

3. The cream formulation as defined in claim 1 wherein the buffer is sodium citrate, potassium citrate, aluminum hydroxide, magnesium hydroxide, an alkali metal hydroxide or mixtures thereof.

4. The cream formulation as defined in claim 1 wherein the non-acidic long chain fatty acid wax is the ethylene glycol ester of a long chain ($C_{18}$–$C_{36}$) fatty acid wax, white wax, carnauba wax or ceresin wax.

5. The cream formulation as defined in claim 1 further including one or more emollients, one or more metal chelating agents, one or more lubricants and one or more antioxidants.

6. The cream formulation as defined in claim 5 wherein the emollient is a mixture of mineral oil and lanolin alcohol, the metal chelating agent is disodium ethylene diamine tetraacetate dihydrate, dipotassium ethylene diamine tetraacetate dihydrate, citrate acid, fumaric acid or malic acid; the lubricant is dimethicone, polyphenylmethylsiloxane or polydimethylsiloxane; and the antioxidant is sodium metabisulfite, butylated hydroxytoluene, butylated hydroxyanisole or sodium ascorbate and the buffer is sodium citrate or potassium citrate.

7. The cream formulation as defined in claim 1 wherein the emulsion stabilizer is glyceryl monostearate, with or without stearic acid, cetyl alcohol, stearyl alcohol or mixtures thereof.

8. The cream formulation as defined in claim 1 wherein the emulsifier is polyoxyethylene glycol 60 sorbitan monostearate, polysorbate 20, polysorbate 65, polysorbate 80 or cetearyl alcohol-ceteareth 20.

9. The cream formulation as defined in claim 1 further including one or more skin conditioners or humectants which is an alkoxylated methyl glucose derivative.

10. The cream formulation as defined in claim 4 wherein the non-acidic long chain fatty acid wax is present in an amount within the range of from about 1 to about 3% by weight.

11. The cream formulation as defined in claim 1 wherein the tipredane is present in an amount within the range of from about 0.05 to about 0.3 % by weight, and the solubilizer for tipredane is propylene glycol present in an amount within the range of from about 10 to about 20 % by weight, and water is present in an amount within the range of from about 40 to about 65% by weight, all of the above % being based on the total weight of the cream formulation.

12. The cream formulation as defined in claim 1 wherein the non-acidic long chain fatty acid wax is present in an amount of within the range of from about 1 to about 3% by weight.

13. The cream formulation as defined in claim 1 wherein the emulsion stabilizer including glyceryl monostearate is present in an amount within the range of from about 7 to about 22 weight %.

14. The cream formulation as defined in claim 1 having the formula

|  | % w/w |
| --- | --- |
| tipredane micronized powder | 0.10% |
| propylene glycol | 15% |
| sodium citrate | 0.5% |
| disodium EDTA dihydrate | 0.005% |
| sodium metabisulfite | 0.02% |
| glyceryl monostearate | 11% |
| cetyl alcohol | 4% |
| ethylene glycol ester of a long chain ($C_{18}$–$C_{36}$) fatty acid wax | 1.5% |
| mineral oil-lanolin alcohol (9:1) | 3% |
| methyl gluceth-20 | 2% |
| polysorbate 60 | 4% |
| silicone fluid | 1% |
| aluminum hydroxide conc. wet gel | 0.4% |
| purified water | 57.5% |

* * * * *

UNITED STATES PATENT AND TRADEMARK OFFICE
CERTIFICATE OF CORRECTION

PATENT NO. : 4,868,169
DATED : Sep. 19, 1989
INVENTOR(S) : Richard L. O'Laughlin et al It is certified that error appears in the above-identified patent and that said Letters Patent is hereby corrected as shown below:

In Claim 6, line 5 thereof, change "citrate" to --citric--.

Signed and Sealed this

Tenth Day of July, 1990

Attest:

HARRY F. MANBECK, JR.

*Attesting Officer*　　　　　*Commissioner of Patents and Trademarks*